(12) United States Patent
Phelps et al.

(10) Patent No.: US 12,178,708 B2
(45) Date of Patent: *Dec. 31, 2024

(54) TALAR BONE PLATE

(71) Applicant: Wright Medical Technology, Inc., Memphis, TN (US)

(72) Inventors: Elizabeth J. Phelps, Collierville, TN (US); Braham K. Dhillon, Memphis, TN (US); Scott A. Armacost, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 621 days.

This patent is subject to a terminal disclaimer.

(21) Appl. No.: 17/236,060

(22) Filed: Apr. 21, 2021

(65) Prior Publication Data

US 2021/0236294 A1  Aug. 5, 2021

Related U.S. Application Data

(63) Continuation of application No. 16/138,056, filed on Sep. 21, 2018, now Pat. No. 11,013,608.

(51) Int. Cl.
*A61F 2/42* (2006.01)
*A61B 17/80* (2006.01)
(Continued)

(52) U.S. Cl.
CPC ........ *A61F 2/4202* (2013.01); *A61B 17/8052* (2013.01); *A61B 17/8061* (2013.01);
(Continued)

(58) Field of Classification Search
CPC ............................. A61F 2/4606; A61F 2/4202
See application file for complete search history.

(56) References Cited

U.S. PATENT DOCUMENTS

| 8,454,665 | B2 | 6/2013 | Sidebotham |
| 9,622,871 | B2 | 4/2017 | Sander |

(Continued)

FOREIGN PATENT DOCUMENTS

| WO | 2017171707 A1 | 10/2017 |
| WO | 2018067143 A1 | 4/2018 |

OTHER PUBLICATIONS

Supplementary Search Report issued in connection with European Patent Application No. 19862980.0, 7 pages, dated May 12, 2022.

(Continued)

*Primary Examiner* — Paul B Prebilic
(74) *Attorney, Agent, or Firm* — Duane Morris LLP

(57) ABSTRACT

A talar bone plate for use with a multi-component ankle prosthesis is disclosed that has a body having a medial side, a lateral side, an upper surface, a lower surface, a medial-anterior end, a lateral-anterior end, a medial-anterior portion that extends out in anterior direction beyond the lateral-anterior side, and a posterior side, where a length between the medial-anterior end and the posterior side is greater than the length between the lateral-anterior end and the posterior side near the lateral side of the body, where the body having at least one elongated screw hole provided in the medial-anterior portion and a plurality of screw holes provided in the area between the at least one elongated screw hole and the posterior side.

8 Claims, 7 Drawing Sheets

(51) Int. Cl.
*A61B 17/86* (2006.01)
*A61F 2/30* (2006.01)
*A61F 2/46* (2006.01)

(52) U.S. Cl.
CPC .......... *A61B 17/86* (2013.01); *A61F 2/30749* (2013.01); *A61F 2/4606* (2013.01); *A61F 2002/30131* (2013.01); *A61F 2002/30604* (2013.01); *A61F 2002/30622* (2013.01); *A61F 2002/4207* (2013.01)

(56) References Cited

U.S. PATENT DOCUMENTS

| | | | |
|---|---|---|---|
| 9,743,965 | B2 | 8/2017 | Kobayashi et al. |
| 11,013,608 | B2* | 5/2021 | Sander ............... A61B 17/8061 |
| 2006/0235396 | A1 | 10/2006 | Sanders et al. |
| 2011/0295324 | A1* | 12/2011 | Donley ............. A61B 17/8014 |
| | | | 606/289 |
| 2014/0277538 | A1 | 9/2014 | Sander |
| 2015/0366597 | A1 | 12/2015 | Kobayashi et al. |
| 2016/0051369 | A1* | 2/2016 | Sander ...................... A61F 2/46 |
| | | | 623/21.18 |
| 2018/0055648 | A1* | 3/2018 | Dhillon ................. A61F 2/4202 |
| 2020/0289283 | A1* | 9/2020 | Sander ................ A61F 2/30771 |
| 2021/0236294 | A1* | 8/2021 | Phelps .................. A61F 2/4202 |

OTHER PUBLICATIONS

Office Action issued in connection with Canadian Patent Application No. 3, 109,510, 3 pages, dated Apr. 26, 2022.

First Examination Report issued in connection with corresponding Australian Patent Application No. 2019344354, dated Aug. 3, 2021, 6 pages.

International Search Report and Written Opinion issued in connection with corresponding International Patent Application No. PCT/US2019/037914, dated Sep. 9, 2019, 9 pages.

\* cited by examiner

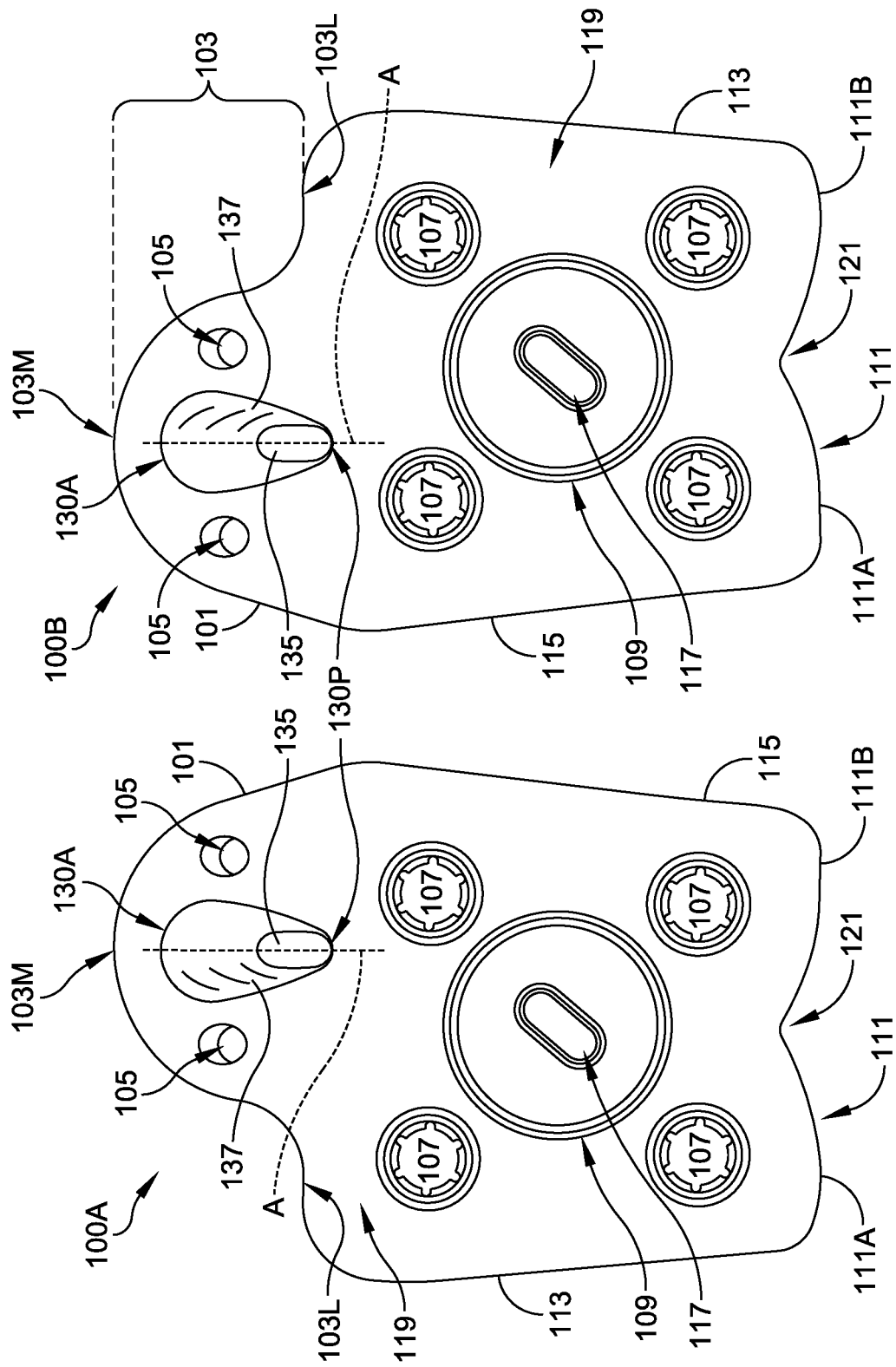

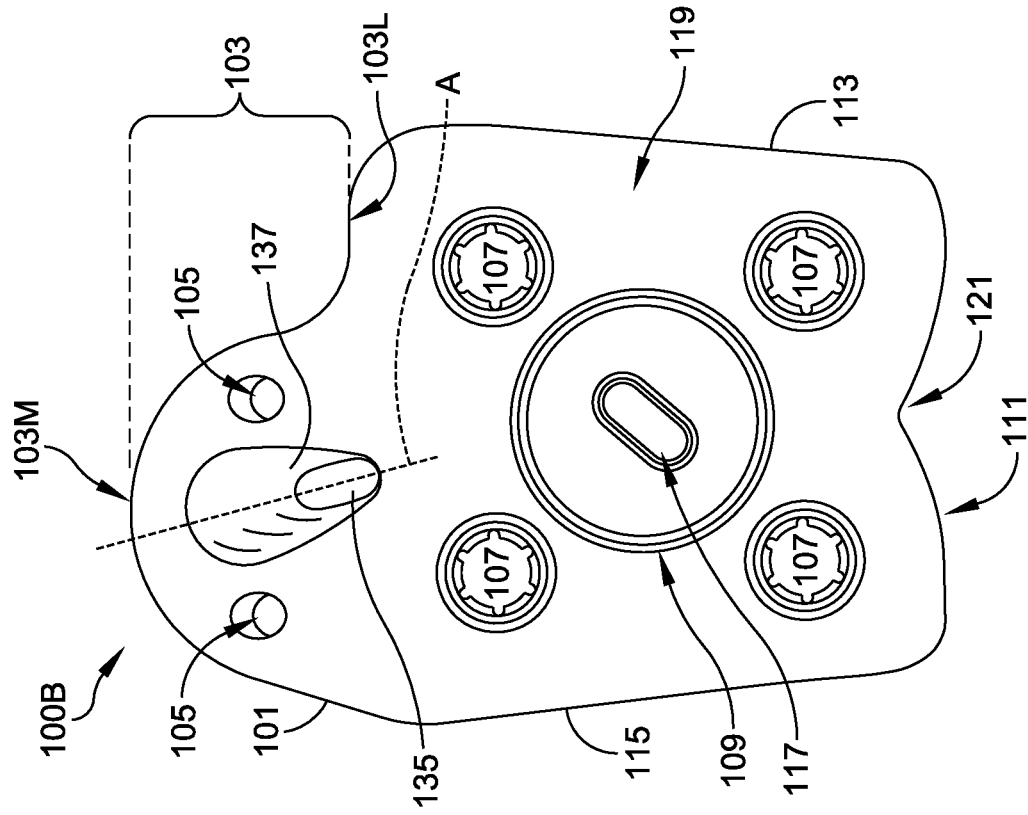
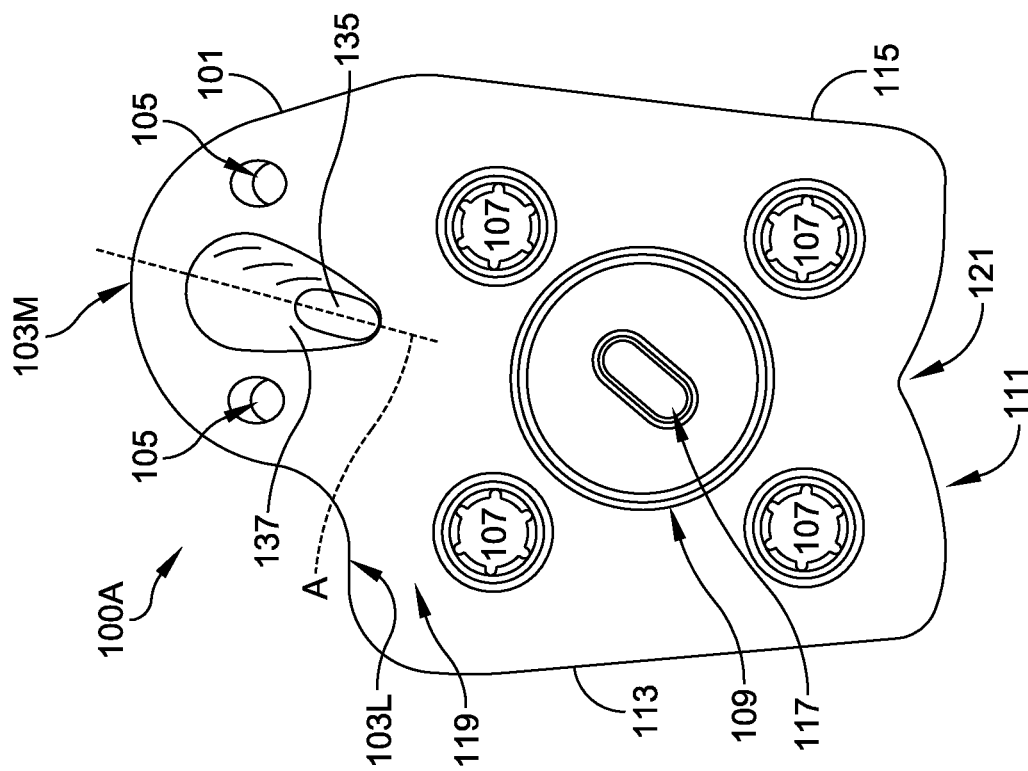

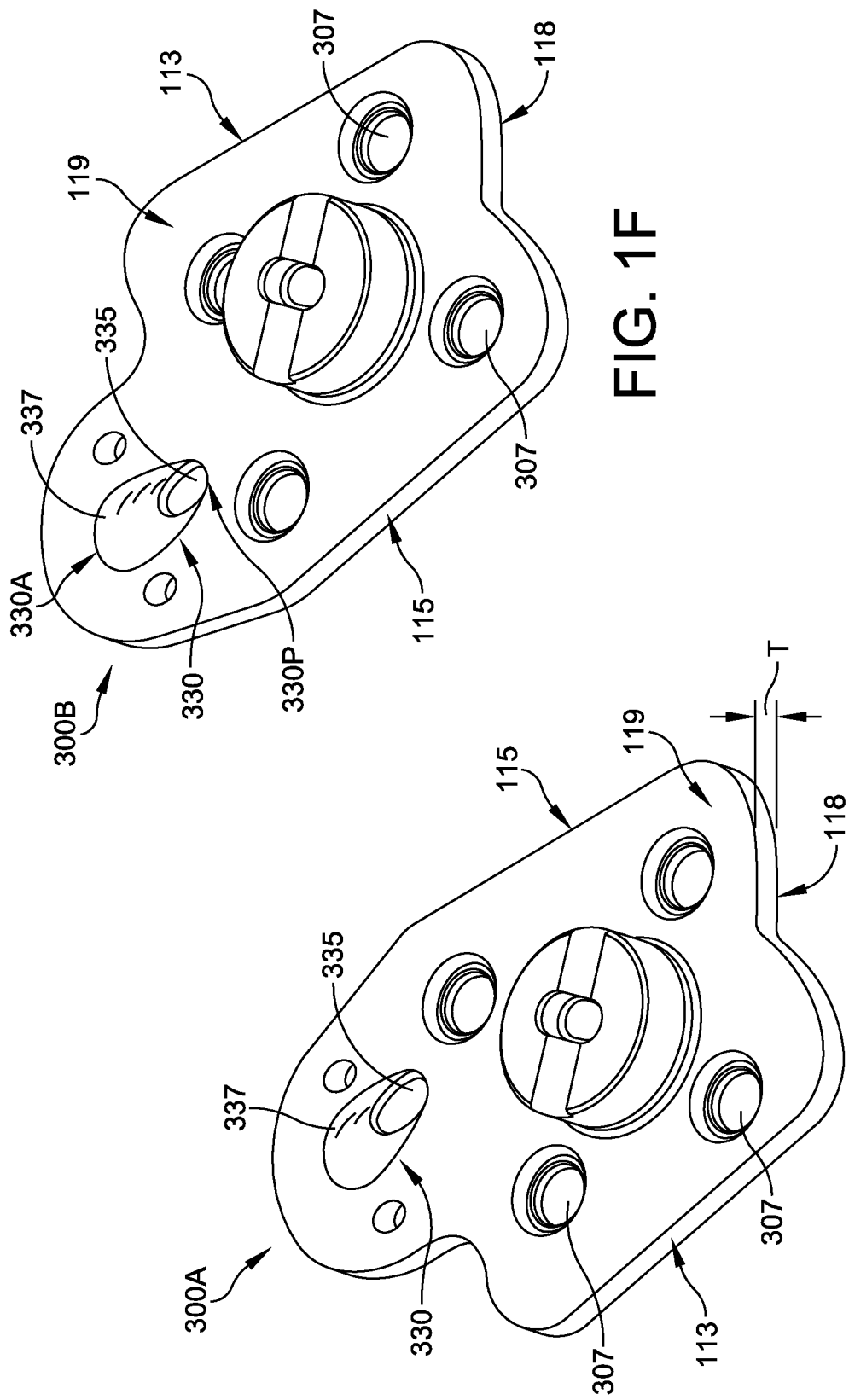

TALAR BONE PLATE

CROSS REFERENCE TO RELATED APPLICATION

This application is a continuation of U.S. patent application Ser. No. 16/138,056, filed Sep. 21, 2018, the disclosure of which is incorporated herein by reference in its entirety.

FIELD OF DISCLOSURE

Disclosed is a bone plate useful in orthopedic surgical applications.

BACKGROUND

Total joint replacements are orthopedic implants for repairing or replacing a natural joint. Examples of common joints that are replaced by a total joint replacement include, but are not limited to, hips, ankles, and shoulders. The ultimate goal with any total joint replacement is to approximate the function and structure of the natural, healthy structures that the implant or prosthesis is replacing.

SUMMARY

In some embodiments, a revision implant component comprises a body including an inner side and an outer side, tapered such that the width of a front side is greater than the width of a back side, the body defining a plurality of screw holes and having a tapered head configured to engage a talar dome component of a multi-component ankle prosthesis.

In some embodiments, a surgical method includes creating an incision in a patient, exposing a multi-component ankle prosthesis implanted in a patient, disassembling at least one component of the multi-component ankle prosthesis, affixing a revision implant component to non-damaged bone using screws, and coupling the revision implant component to a talar dome of the multi-component ankle prosthesis. The revision implant component has a body including a head configured to engage a feature of a component of the multi-component ankle prosthesis for coupling the revision implant component to the component of the multi-component ankle prosthesis.

BRIEF DESCRIPTION OF THE DRAWINGS

FIGS. 1A and 1B are top-down views of a left and right ankle talar plates, respectively, in accordance with some embodiments.

FIGS. 1C and 1D are top-down views of a left and right ankle talar plates, respectively, in accordance with additional embodiments.

FIGS. 1E and 1F are isometric views of the left and right ankle talar plates of FIGS. 1A and 1B, respectively.

DETAILED DESCRIPTION

Figure 2B:
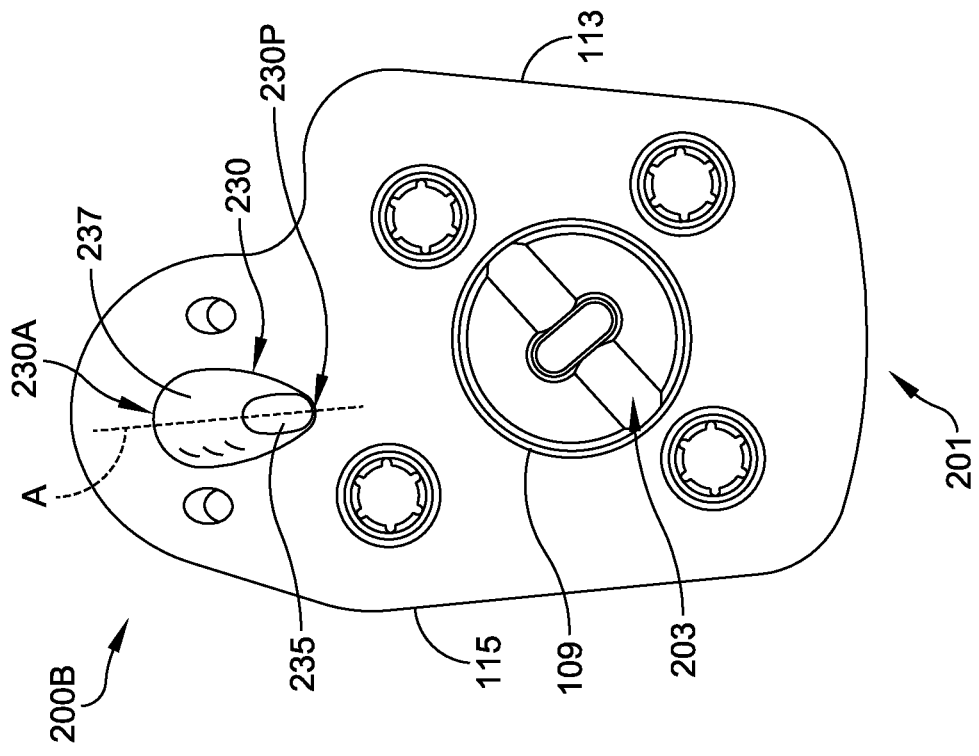
FIGS. 2A and 2B are top-down views of a left and right ankle talar plates, respectively, in accordance with some other embodiments.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Bone plates are disclosed herein are designed to span across a navicular-talar joint and attach to the talar bone and the navicular bone for compressing the navicular-talar joint. The bone plates can also be positioned to span across a talar neck fracture in the talar bone and attach to the two portions of the talar bone on either side of the crack.

A combination of an elongated screw hole provided on the anterior portion of the bone plate and a plurality of screw holes provided on the remaining portion of the bone plate allow the use of the bone plate to reduce and stabilize the navicular bone and the talus bone of a navicular-talar joint or reduce and stabilize the two portions of a talar neck fracture. The elongated screw hole is configured to receive a screw such as a lag screw or a non-locking screw. The bone plates can be useful as part of a revision ankle implant system. The direction of the elongation for the elongated screw hole determines the direction of the bone or joint reduction. Thus, the elongated screw hole can be designed to have a desired elongation direction. In some embodiments, the elongated screw hole can be configured to further include a ramped or a sloped portion so that the elongated screw hole functions as a compression slot.

FIGS. 1A and 1B are top-down views of examples of the bone plates that are configured to be used in orthopedic treatment of talar bones. FIG. 1A shows a left ankle talar plate 100A and FIG. 1B shows a right ankle talar plate 100B. Because the left ankle talar plate 100A and the corresponding right ankle talar plate 100B are symmetrical and mirror images of each other, the following description of the left ankle talar plate 100A is applicable to the right ankle version 100B. The analogous structures in the talar plates are labeled using the same reference numbers.

The left ankle talar plate 100A comprises a body 101 having a medial side 115, a lateral side 113, a medial-anterior end 103M near the medial side, a lateral-anterior end 103L near the lateral side 113, posterior side 111, an upper surface 119, and a lower surface 118 (shown in FIGS. 1E and 1F). The length between the posterior side 111 of the body 101 to the medial-anterior end 103M is greater than the length between the posterior side 111 of the body 101 to the lateral-anterior end 103L. Thus, as shown in FIG. 1A, the left ankle talar plate 100A has a mitten shaped outline with a medial-anterior portion 103 that extends further out in the anterior direction beyond the lateral-anterior end 103L.

The talar plate 100A is provided with a plurality of screw holes 107 for receiving bone screws for securing the talar plate 100A to a talus. The talar plate 100A is shaped and dimensioned to substantially align with a top surface of a resected talus. The body 101 also includes a tapered head 109 protruding from the upper surface 119 for connecting to a talar dome implant 50 (see FIG. 3). In some embodiments, the body 101 is shaped and dimensioned to substantially align with a bottom surface of the talar dome implant 50.

The medial-anterior portion 103 of the talar plates 100A and 100B is provided with an elongated screw hole 135 for securing the medial-anterior portion 103 to a navicular bone so that the talar plate 100A can be used for reducing or compressing the navicular-talar joint.

In this embodiment, the elongated screw hole 135 is located on the medial-anterior portion 103 so that when the talar plate 110A is positioned over a navicular-talar joint the elongated screw hole 135 is positioned over the navicular bone and the central axis A of the elongated screw hole 135 is generally oriented from the navicular bone toward the talus. The elongation direction of the elongated screw hole 135 allows a bone screw inserted through the elongated screw hole 135 and threaded into the navicular bone to compress the navicular bone toward the talus, thus reducing the navicular-talar joint.

The direction of the compression is represented by the central axis A of the elongated screw hole 135. Therefore, a plurality of talar plates can be provided with each talar plate having the elongated screw hole 135 at different orientations and allow the surgeon to select a talar plate that will provide the necessary compression direction for a given patient. For example, FIGS. 1A, 1B and the FIGS. 1C, 1D show examples of talar plates 100A, 100B, having the elongated screw hole 135 oriented in different direction. The central axes A of the elongated screw hole 135 in the talar plates in FIGS. 1C, 1D are at a different angle with respect to the medial sides 115, for example, compared to the central axes A of the elongated screw hole 135 in the talar plates shown in FIGS. 1A, 1B.

Figure 3A:
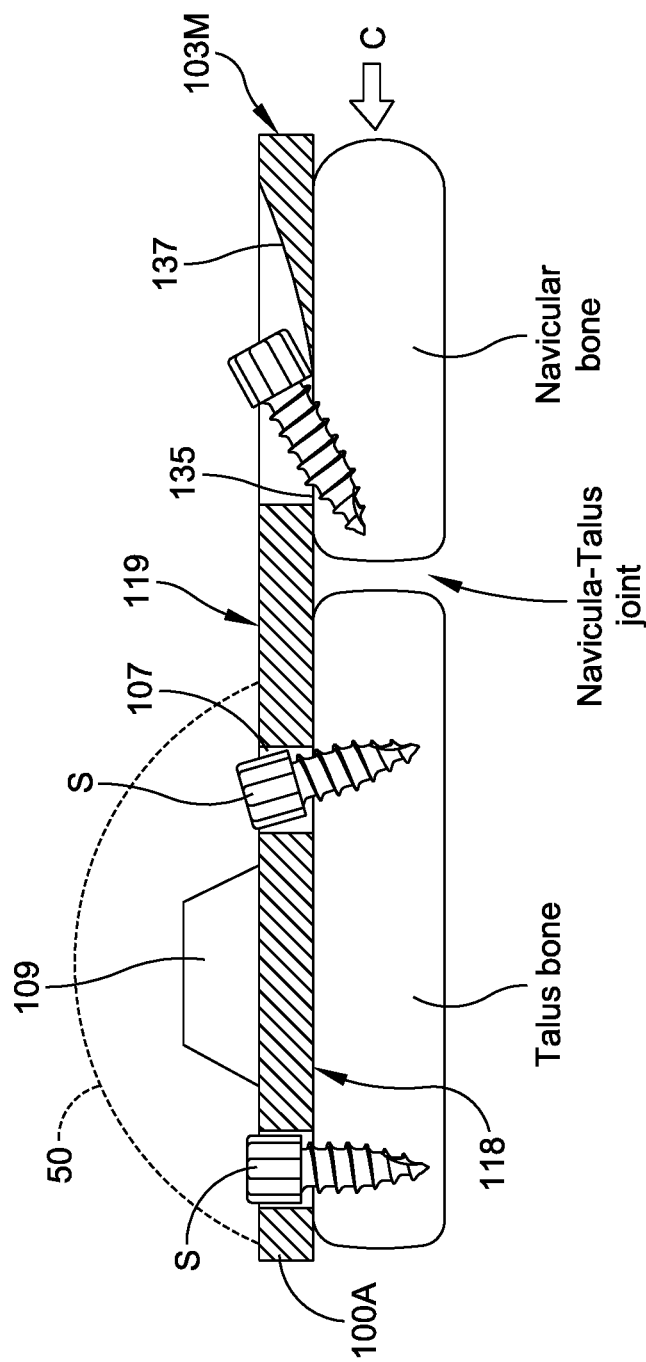
FIG. 3A is a schematic side-view of the placement of the talar plate in relation to a navicular-talus joint accordance with some embodiments.

FIG. 3A is a schematic illustration showing a side-view of the talar plate 100A positioned in place over a talus bone and a navicular bone across the navicular-talar joint. The elongated screw hole 135 is provided near the anterior side 103 of the talar plate 100A and presides over the navicular bone. The bone screw inserted through the elongated screw hole 135 and threaded into the navicular bone compresses the navicular bone in the direction represented by the arrow C, thus reducing the navicular-talar joint.

Figure 3B:
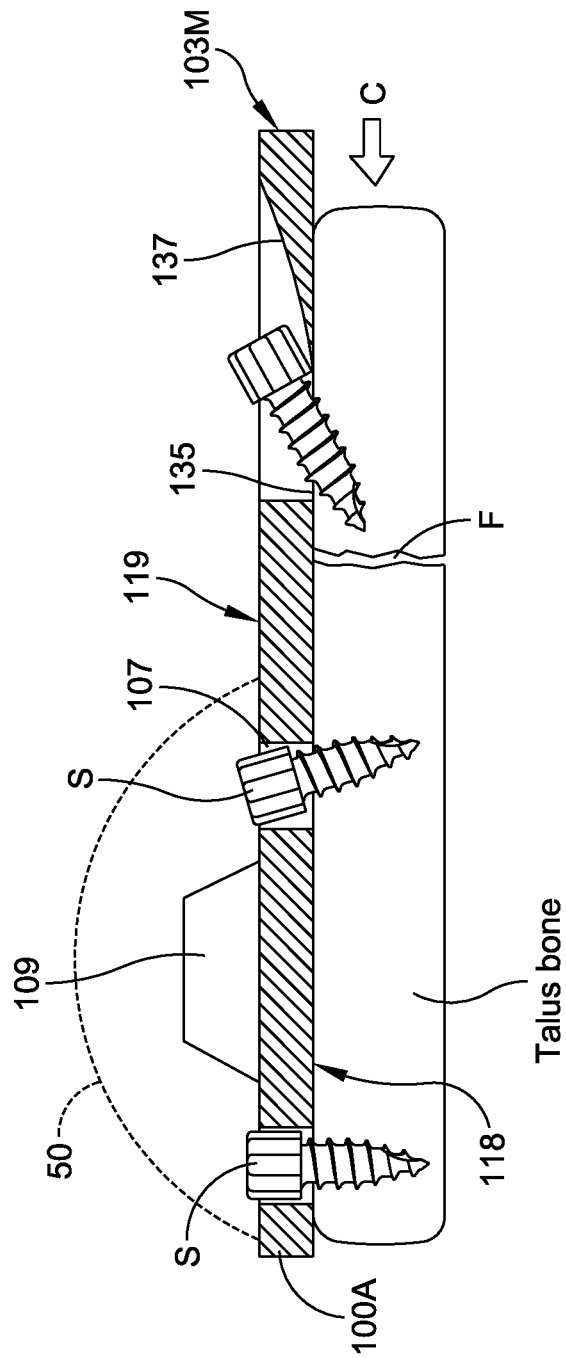
FIG. 3B is a schematic side-view of the placement of the talar plate in relation to a talus bone with a fracture in the talar neck.

In other embodiments, the talar plates 100A, 100B an be used to stabilize a fractured talar neck. Referring to FIG. 3B, in this configuration, the talar plate 100A is placed on a talus bone to span over a fracture in the talar neck. The talar plate 100A is positioned over the fracture F in the talar neck so that the portion of the talar plate's body 101 having the plurality of screw holes 107 is positioned on one side of the fracture and the medial-anterior portion 130, specifically the elongated screw hole 135 provided on the medial-anterior portion 130, is positioned on the opposite side of the fracture. The talar plate is secured to the first side of the talar bone by inserting bone screws through the plurality of screw holes 107. Then, the medial anterior portion 130 is secured to the talar neck on the opposite side of the fracture F by a bone screw threaded into the talar neck through the elongated screw hole 135.

As shown in FIGS. 1A-1F, the elongated screw hole 135 can be provided with a ramped or a sloped portion 137 to further enhance the compression function of the elongated screw hole 135. The sloped portion 137 slopes downward (i.e. sloped toward the lower surface 118 of the bone plate) starting from the upper surface 119 of the anterior end 130A of the sloped portion 137 toward the elongated screw hole 135 at the posterior end 130P of the sloped portion 137.

In some embodiments, the shape of the body 101 of the talar plates 100A, 100B is configured to match the shape of the talar dome implant. In other embodiments, the shape of the body 101 is configured to match the shape of the talus. In the example talar plate 100A, the anterior side 103 has a bulbous shape and the posterior side 111 has a sulcus or a groove 121. The groove 121 is defined by a first convex curve 111A and a second convex curve 111B. In some embodiments of the talar plates, the posterior side 111 has a straight, curved, or bulbous edge shape 201 as shown in the talar plates 200A and 200B shown in FIGS. 2A and 2B. Similarly, in some embodiments anterior side 103 has a straight, curved, or grooved shape so as to match the shape of a talar dome implant or the talus.

The medial side 113 and the lateral side 115 are tapered from anterior side to the posterior side, such that the body 101 is narrower at the posterior side 111. The taper of the medial side 113 and the lateral side 115 is configured to fill the bone voids that may be present in some ankles and rest on the remaining talar bone in a revision ankle application.

In some embodiments, the screw holes 107 are non-locking type and can include polyaxial locking tabs as shown in the examples illustrated in FIGS. 1A-1D. In some embodiments, the screw holes 107 are locking type and are threaded to be used with locking screws having threaded heads. FIGS. 1E and 1F show examples of such threaded screw holes 307.

In some embodiments, the body 101 defines at least one wire hole 105 for wires. The wire holes 105 assist in the proper placement of the revision talar plate during surgery. Wire holes 105 can be configured to receive k-wires or similar surgical tools to ensure that the revision talar plate is placed in the proper location as determined by a surgeon and as guided by surgical instrumentation.

The tapered head 109 has a tapered shape and is configured for engaging the talar dome implant 50. In some embodiments, the tapered head 109 engages the talar dome implant 50 by an interference connection. A tapered recess in the talar dome implant would receive the tapered head 109, and an impact connection is made between the talar dome implant and the tapered head 109. In some embodiments, the taper on the tapered head 109 is a Morse taper. In some embodiments, the tapered head 109 additionally defines a recess 117.

In still further embodiments, the tapered head 109 comprises "timed threads" that are configured such that when the threaded tapered head 109 and threaded talar dome implant are properly connected, a longitudinal passageway is in alignment. Traditional threaded connections accept varying amounts of torque and respond with varying alignments. The timed threads ensure a proper connection and a specific alignment so long as the applied torque is within a predetermined range.

Referring to FIG. 1E, in some embodiments, the talar plate 100A has a thickness T, as measured from the upper surface 119 to the substantially parallel lower surface 118, is configured to match the thickness of bone loss. The thickness T is labeled in FIG. 1E. In other embodiments, the thickness of the talar plate 100A is configured to match the thickness required for proper support of a talar dome implant. In other embodiments, the peripheral edge of the talar plate can be angled or tapered in a desired direction along the length of the talar plate.

FIGS. 1E and 1F are isometric views of left ankle and right ankle talar plates 300A and 300B according to some embodiments. The left ankle talar plate 300A is substantially the same as the left ankle talar plate 100A described above except that the talar plate 300A is provided with a plurality of screw holes 307 that are locking type. In this embodiment, the screw holes 307 are threaded or include a deformable region adjacent to the holes designed to contact the threaded head of a locking screw. The talar plates 300A and 300B each has an elongated screw hole 335 that is similarly structured as the elongated screw hole 135 described above. The elongated screw hole 335 has an elongated shape with a central axis A and comprises a sloped portion 337 that slopes downward (i.e. sloped toward the lower surface 118) starting from the anterior end 330A of the sloped portion 337 and terminating with the elongated screw hole 335 at the posterior end 330P of the sloped portion 337. As with the right ankle talar plate 100B, the right ankle talar plate 300B is the mirror image of the talar plate 300A and all of the remaining structures are the same.

Figure 2A:
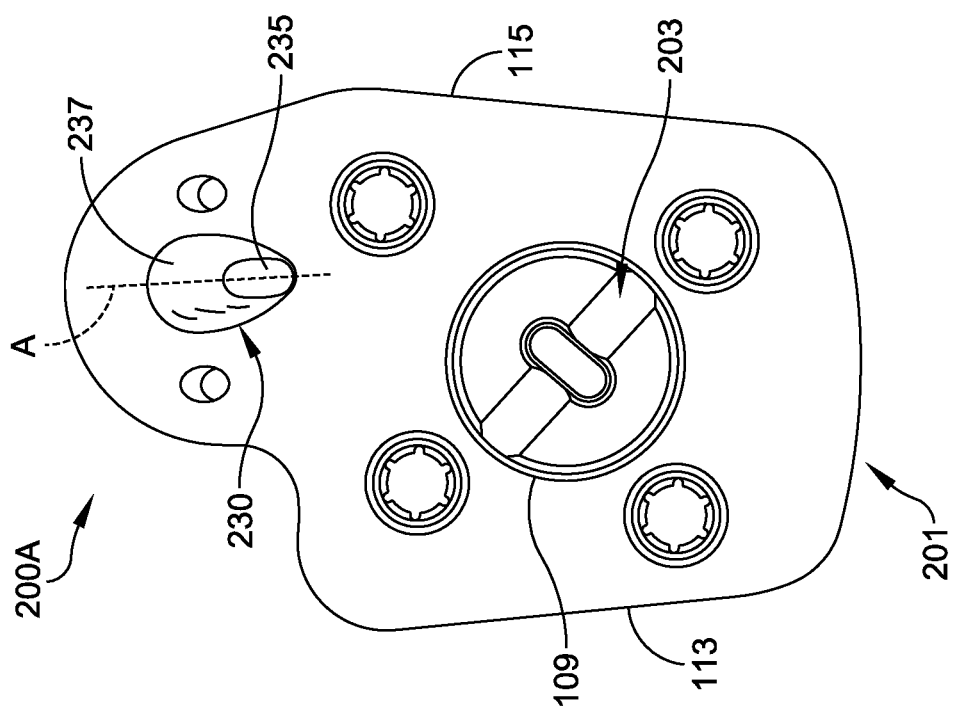

FIGS. 2A and 2B illustrate left ankle and right ankle talar plates 200A and 200B, respectively, in accordance with some embodiments. FIG. 2A is a top view of talar plate 200A. The left ankle talar plate 200A and the right ankle talar plate 200B are substantially the same as the left ankle talar plate 100A described above. However, the talar plates 200A and 200B have a curved posterior side 201 rather than the grooved posterior sides 111. The talar plates 200A and 200B each has an elongated screw hole 235 that is similarly structured as the elongated screw hole 135 described above. The elongated screw hole 235 has an elongated shape with a central axis A and comprises a sloped portion 237 that slopes downward (i.e. sloped toward the lower surface 118) starting from the anterior end 230A of the sloped portion 237 towards the elongated screw hole 235 at the posterior end 230P of the sloped portion 237.

Additionally, the tapered head 109 can have a notch 203 provided therein that is sized and configured to receive a screw driver or other elongate tool for removing the talar plate 200A, 200B. The talar plates 200A and 200B are mirror images of each other as they are for left ankle and right ankle applications, respectively.

FIG. 3B illustrates a second example of a revision implant component 300B in accordance with some embodiments. Revision implant component 300B is a mirror image of revision implant component 300A, and is therefore configured for use with the right ankle joint of a patient.

In some embodiments, one or more of the bone plates of the present disclosure, such as the talar plate examples described above with reference to FIGS. 1A-1F, 2A, 2B, and 3, are provided in a surgical kit. Each of the provided bone plates may have a varying shape or thickness (as measured from the upper surface to a substantially parallel back surface—see the thickness T in FIG. 1E). By providing varying shapes, thicknesses, and angles, the kit allows a surgeon to conduct an intraoperative determination of the best-fitting bone plate for use with a multi-component ankle prosthesis.

A surgical kit according to an embodiment, comprises one or more of the any of the embodiments of the bone plates described herein for use with a multi-component ankle prosthesis.

The talar bone plates described herein can be used in revision ankle systems or in primary ankle implant systems. The use of the talar bone plates of the present disclosure allows the bone fusion to be done at the same time as the revision.

Referring to FIG. 3A, in the example where the talar bone plate 100A is applied to span across the navicular-talar joint, the compression bone screw used in the elongated screw hole 135 on the talar bone plate 100A of the present disclosure can thread into and through the navicular bone and extend across the navicular-talus joint into the talus bone. The main body portion (the part of the talar bone plate 100A other than the medial-anterior portion 103) of the talar bone plate 100A is secured to the talus bone by screws threaded through the plurality of screw holes 107. Then, a compression bone screw is inserted into the elongated screw hole 135 provided on the medial-anterior portion 103 of the talar bone plate 100A and threads into and through the navicular bone, across the navicular-talus joint and into the talus bone and either fuse the two bones together or reduce the navicular-talus joint space.

Referring to FIG. 3B, in the example where the talar bone plate 100A is applied to the talar bone to span across a fracture F near the talar neck, the talar bone plate 100A would be applied so that the medial-anterior portion 103 of the talar bone plate having the elongated screw hole 135 is on the talar neck side of the fracture F. The main body portion of the talar bone plate 100A is secured to the talar bone by screws threaded through the plurality of screw holes 107 in the main body portion. Then, a compression bone screw is inserted into the elongated screw hole 135 provided on the medial-anterior portion 103 of the talar bone plate and threaded into the talar neck portion to compress the two portions of the talar bone and reduce and stabilize the fracture F.

In some embodiments, each of the one or more talar bone plates provided in the surgical kit can further comprise a tapered head configured to engage a talar dome implant component of the multi-component ankle prosthesis, provided on the upper surface. The tapered head can be shaped and dimensioned as a Morse taper.

Figure 4:
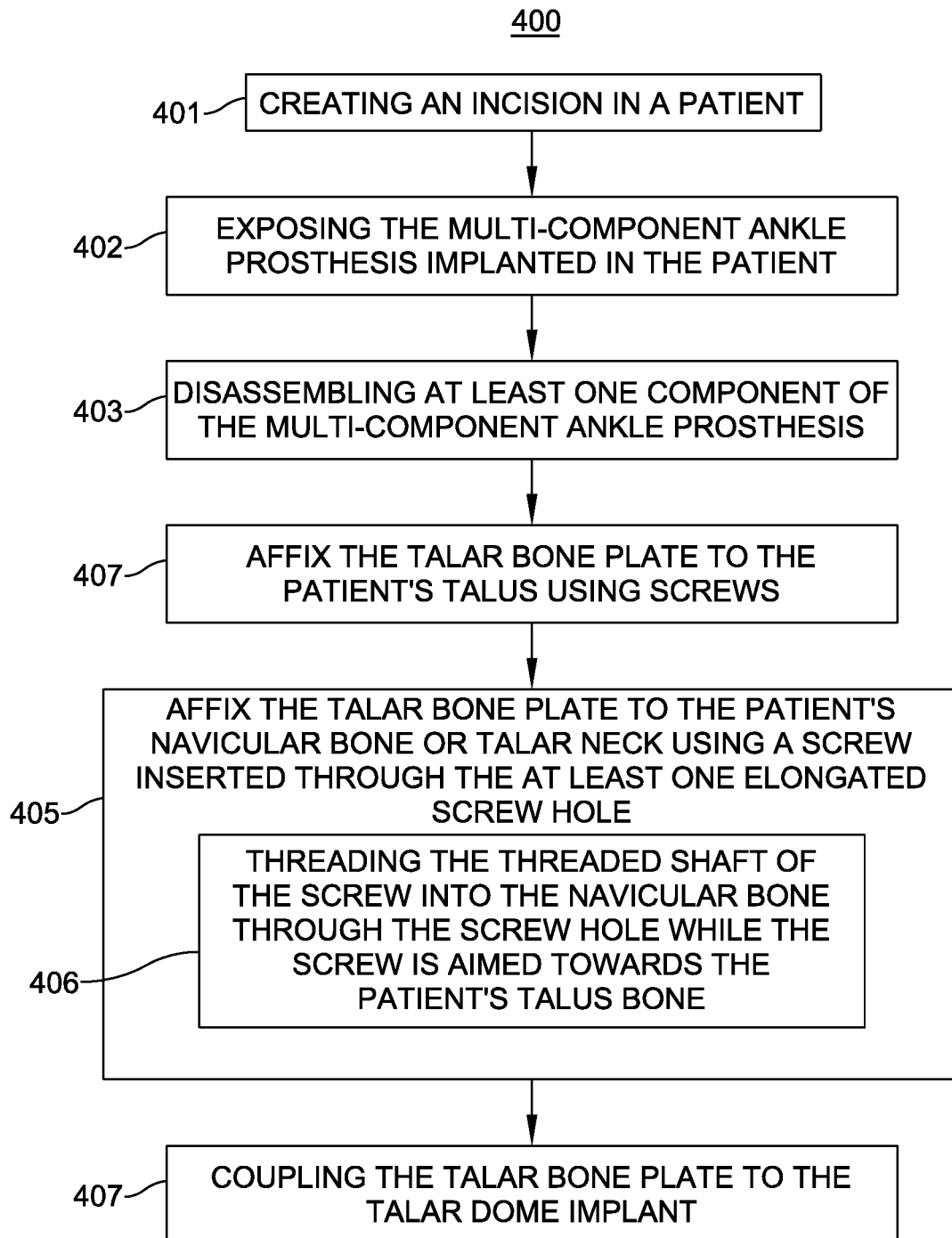
FIG. 4 is a flow diagram of a method in accordance with some embodiments.

A surgical method of using the talar bone plate 100A of the present disclosure is also disclosed. The method is summarized in the flow chart 400 of FIG. 4. At block 401, the method includes making an incision in a patient in proximity of the patient's ankle. At block 402, the multi-component ankle prosthesis which was previously installed in the patient is exposed through the incision. At block 403, a first component or at least one component of the multi-component ankle prosthesis is disassembled and removed from the patient. During a revision procedure, a multi-component ankle prosthesis that was previously implanted in the patient may be partially or completely disassembled. For example, if the multi-component prosthesis is a talar prosthesis, then the talar dome can be decoupled from talar stem by disengaging the Morse taper coupling. When completely disassembled, the entire multi-component prosthesis is removed from the patient. At block 404, the talar bone plate is affixed to the patient's talus using screws utilizing the screw holes such as 107, 307 described above. At block 405, the talar bone plate is affixed to the patient's navicular bone using a screw inserted through the at least one elongated screw hole 135, 235, 335 described above. The head of the screw engages with the sloped portion 137, 237, 337 of the elongated screw hole and applies compression force on the navicular bone to either reduce the navicular-talus joint or fuse the navicular bone and the talus bone.

According to some embodiments, the at least one elongated screw hole 135 on the talar bone plate 100A is structured as described above and the affixing the talar bone plate to the patient's navicular bone using a screw inserted through the at least one elongated screw hole 135 includes threading the threaded shaft of the screw into the navicular bone through the elongated screw hole 135 while the screw is positioned at an angle so that the threaded shaft of the screw is aimed towards the patient's talus bone (see block 406).

According to some embodiments, the talar bone plate further comprises the tapered head configured to engage a talar dome implant component of the multi-component ankle prosthesis and the surgical method further comprises coupling the talar bone plate to the talar dome implant by engaging the tapered head to the talar dome implant (see block 407).

According to some embodiments of the surgical method, after affixing the main portion of the talar bone plate 100A to the patient's talus using screws, the medial-anterior portion 103 of the talar bone plate is affixed to a talar neck portion of the talus on an opposite side of a talar neck fracture F using a screw inserted through the at least one elongated screw hole 135.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

We claim:

1. A surgical method for use of a talar bone plate with a multi-component ankle prosthesis comprising:
    providing a talar bone plate having a body including a medial side, a lateral side, an upper surface, a lower surface, a medial-anterior end, a lateral-anterior end, a medial-anterior portion that extends out in an anterior direction beyond the lateral-anterior end, and a posterior side with a length between the medial-anterior end and the posterior side of the body being greater than the length between the lateral-anterior end and the posterior side, and further with the body having at least one elongated screw hole located at a posterior end, the body defining an elongated sloped surface that slopes downwardly from the upper surface at the medial-anterior end toward the lower surface and the elongated screw hole provided in the medial-anterior portion and a plurality of screw holes provided in the area between the at least one elongated screw hole and the posterior side;
    creating an incision in a patient in proximity of the patient's ankle;
        exposing the multi-component ankle prosthesis implanted in the patient;
        disassembling at least one component of the multi-component ankle prosthesis;
        affixing the talar bone plate to the patient's talus using screws; and
        affixing the medial-anterior portion of the talar bone plate to the patient's navicular bone using a screw inserted through the at least one elongated screw hole such that the engagement of the screw with the elongated sloped surface applies a force to the talar bone plate that enhances the compression function of the at least one elongated screw hole.

2. The surgical method of claim 1, wherein the talar bone plate further comprises a tapered head configured to engage a talar dome implant component of the multi-component ankle prosthesis and the surgical method further comprising: coupling the talar bone plate to the talar dome implant by engaging the tapered head to the talar dome implant.

3. A surgical method of claim 1, comprising:
    creating an incision in a patient anteriorly of the patient's ankle;
    exposing the multi-component ankle prosthesis implanted in the patient;
    disassembling multiple components of the ankle prosthesis; and
    affixing the talar bone plate to the patient's talus using screws.

4. A surgical method of claim 1, wherein the at least one elongated screw hole has a sloped portion that has an elongated shape with an anterior end and a posterior end,
    wherein the elongated screw hole is located at the posterior end, and
    wherein sloped portion slopes downward starting from the upper surface at the anterior end towards the elongated screw hole.

5. A surgical method of claim 1, further comprising a tapered head configured to engage a talar dome implant component of the multi-component ankle prosthesis, provided on the upper surface.

6. A surgical method of claim 1, wherein the posterior side of the body has first and second convex curves separated by a groove.

7. A surgical method of claim 1, wherein the body is tapered such that the width of an anterior side is greater than the width of the posterior side.

8. A surgical method of claim 1, wherein the body is shaped and dimensioned to substantially align with a top surface of a resected talus.

* * * * *